United States Patent
Pearson et al.

(10) Patent No.: US 9,528,864 B2
(45) Date of Patent: Dec. 27, 2016

(54) SILT CONTROL IN FLUID NETWORKS

(71) Applicant: Rubicon Research Pty Ltd, Hawthorn, Victoria (AU)

(72) Inventors: Damien Vernon Pearson, Kew East (AU); Reece Joseph Tyrrell, Hawthorn (AU); Gordon John Bish, Hawthorn (AU)

(73) Assignee: RUBICON RESEARCH PTY LTD, Victoria (AU)

( * ) Notice: Subject to any disclaimer, the term of this patent is extended or adjusted under 35 U.S.C. 154(b) by 46 days.

(21) Appl. No.: 14/404,947

(22) PCT Filed: May 30, 2013

(86) PCT No.: PCT/AU2013/000570
§ 371 (c)(1),
(2) Date: Dec. 1, 2014

(87) PCT Pub. No.: WO2013/177626
PCT Pub. Date: Dec. 5, 2013

(65) Prior Publication Data
US 2015/0143917 A1    May 28, 2015

(30) Foreign Application Priority Data
May 30, 2012   (AU) ................................ 2012902251

(51) Int. Cl.
*G01F 1/00*    (2006.01)
*B08B 17/02*   (2006.01)
(Continued)

(52) U.S. Cl.
CPC ................. *G01F 1/00* (2013.01); *B08B 17/02* (2013.01); *E03B 7/07* (2013.01); *F17D 3/18* (2013.01);
(Continued)

(58) Field of Classification Search
CPC ................ G01F 1/66; G01F 1/00; G01F 1/86; G01F 17/00
(Continued)

(56) References Cited

U.S. PATENT DOCUMENTS

| 4,300,401 | A | | 11/1981 | Pedersen |
| 4,485,450 | A | * | 11/1984 | Characklis ............. G01N 11/14 702/41 |
| 4,912,332 | A | * | 3/1990 | Siebel ....................... F17D 5/00 250/341.1 |
| 5,780,747 | A | | 7/1998 | Soo |

(Continued)

FOREIGN PATENT DOCUMENTS

| CN | 101198841 | 6/2008 |
| GB | 2029030 | 3/1980 |

(Continued)

OTHER PUBLICATIONS

International Application No. PCT/AU2013/000570, International Search Report mailed Aug. 6, 2013.
International Application No. PCT/AU2013/000570, Written Opinion mailed Aug. 6, 2013.
(Continued)

*Primary Examiner* — Jewel V Thompson
(74) *Attorney, Agent, or Firm* — Sheppard Mullin Richter & Hampton LLP

(57) ABSTRACT

The invention relates to a method of detecting a buildup of silt in a pipe or open channel of a fluid flow network. The pipe or open channel has a system with at least one set of velocity sensors to measure flow velocities at predetermined horizontal levels. The method includes the steps of computing flow using measured flow velocities and cross-sectional areas for each flow layer, summing the flows to provide a total flow, monitoring the measured flow velocities and storing the measured flow velocities to detect any ongoing reduction in flow velocity of at least a lowermost velocity sensor to provide an indication of a buildup of silt in the pipe or open channel.

10 Claims, 9 Drawing Sheets

(51) Int. Cl.

| | |
|---|---|
| *E03B 7/07* | (2006.01) |
| *F17D 3/18* | (2006.01) |
| *F17D 5/00* | (2006.01) |
| *G01F 1/66* | (2006.01) |
| *G01F 1/74* | (2006.01) |
| *G01N 11/00* | (2006.01) |
| *G01F 23/296* | (2006.01) |
| *G01M 1/00* | (2006.01) |
| *G01F 15/07* | (2006.01) |

(52) U.S. Cl.
CPC ................ *F17D 5/00* (2013.01); *G01F 1/002* (2013.01); *G01F 1/667* (2013.01); *G01F 1/74* (2013.01); *G01F 23/2961* (2013.01); *G01M 1/00* (2013.01); *G01N 11/00* (2013.01); *G01F 15/07* (2013.01); *G01F 23/2962* (2013.01)

(58) Field of Classification Search
USPC .............. 73/861.27, 861, 861.02; 702/50, 45
See application file for complete search history.

(56) References Cited

U.S. PATENT DOCUMENTS

| | | | |
|---|---|---|---|
| 5,987,997 A | 11/1999 | Roskam et al. | |
| 6,781,148 B2* | 8/2004 | Kubota | H01L 51/5253 |
| | | | 257/40 |
| 6,871,148 B2 | 3/2005 | Morgen et al. | |
| 7,330,797 B2* | 2/2008 | Bailey | G01F 1/74 |
| | | | 702/100 |
| 2009/0211330 A1 | 8/2009 | Froehlich et al. | |

FOREIGN PATENT DOCUMENTS

| | | |
|---|---|---|
| JP | 2005321314 | 11/2005 |
| WO | 2011020143 | 2/2011 |

OTHER PUBLICATIONS

Chinese Patent Application No. 201380036050.9, Office Action mailed Apr. 6, 2016.

* cited by examiner

SILT CONTROL IN FLUID NETWORKS

CROSS-REFERENCE TO RELATED APPLICATIONS

This application is a national stage application pursuant to 35 U.S.C. §371 of International Application No. PCT/AU2013/000570, filed May 30, 2013, which claims priority to Australian Patent Application No. 2012902251, filed May 30, 2012, the disclosures of which are hereby incorporated by reference herein.

FIELD OF THE INVENTION

The present invention relates to the detection and measurement of silt depth in a fluid flow network.

BACKGROUND OF THE INVENTION

In our International Patent Application No. PCT/AU2010/001052 (published as WO 2011/020143), the entirety of which is herein incorporated, there are disclosed flow meter assemblies and methods of flow measurements.

In traditional flow measurement technologies (such as electromagnetic flow meters) flow is determined by multiplying the known cross-sectional area of a pipe or channel by the average velocity passing through this known cross section. Typically, there is one flow velocity sensor, and the average velocity is determined using this sensor. Flow is derived by multiplying the total cross sectional area of the said pipe or channel by this average velocity. The problem with this measurement technology is that the use of the average velocity multiplied by the total cross sectional area allows significant errors to occur. Unfortunately, silt may build up in the pipe or channel, reducing the cross-sectional area of the pipe or channel. Because the area through which fluid flows in a silted pipe or channel is reduced relative to a clean pipe or channel, the area assumed in the flow measurement calculation is greater than the true cross-sectional area through which the fluid flows. The flow continues to be calculated by multiplying the average velocity by the assumed cross-sectional area of the conduit. This will result in significant errors in determining the flow rate.

The above problems were lessened using the systems disclosed in our International Patent Application No. PCT/AU2010/001052. This system provided a flow meter that uses the 'time of flight' acoustic or 'transit time' method to measure multiple velocities at multiple slices through the cross-sectional area of the flow meter. The system provided a multi-path analysis of velocity across a pipe or channel at a number of horizontally disposed layers. The method of computing flow is to first compute the velocity within each discrete horizontal layer. The velocity within each layer is then multiplied by the width and the height of that layer to determine the flow passing through that layer. The flows passing through each layer are then summed to determine the total flow passing through the cross-section of the meter. The flow through the conduit is therefore the sum of each discrete flow layer. Such a calculation, using multiple sensors, provided an accurate determination of flow.

When silt accumulates, the cross sectional area of the conduit changes. At the same time, the actual velocity profile within this cross-section changes. Because the flow velocity at the silt-water interface is zero, the bottom path velocity decreases. To maintain the same flow rate through the pipe or channel, the remaining path velocities must increase slightly. Because multiple velocity measurements are made at known elevations within the meter cross section, the actual velocity profile is used to calculate the flow rate. The error in the calculated flow will be reduced compared with the traditional flow measurement technology previously described which uses a single velocity measurement to compute flow.

OBJECTS OF THE INVENTION

It is an object of the present invention to provide a method of detecting silt in a fluid flow network.

A further object of the present invention is to enhance the accuracy of measurement of fluid flow in a fluid flow network under arduous conditions.

SUMMARY OF THE INVENTION

The present invention in one embodiment provides a method of detecting a buildup of silt in a pipe or open channel of a fluid flow network, said pipe or open channel having at least one set of vertically spaced velocity sensors to measure flow velocities at predetermined horizontal levels, said method including the steps of computing the flow using the measured flow velocities and cross-sectional areas for each flow layer, and summing said flows to provide a total flow at said at least one set of vertically spaced velocity sensors, monitoring said measured flow velocities and storing said flow velocities to detect any ongoing reduction in the flow velocity of at least the lowermost velocity sensor at a selected total flow whereby said ongoing reduction provides an indication of a buildup of silt in said pipe or open channel.

The invention may also provide a method of measuring a build up of silt in a pipe or open channel of a fluid flow network, said pipe or open channel having a system having at least one set of vertically spaced velocity sensors to measure flow velocities at predetermined horizontal levels, said method including the steps of monitoring said measured flow velocities and storing said flow velocities, calibrating said system to provide a silt-free velocity profile of said at least one set of vertically spaced velocity sensors and a plurality of velocity profiles at predetermined silt depths to allow a relationship to be calculated between silt depth and the flow velocity of at least the lowermost velocity sensor at a selected total flow as the reduction in the flow velocity of said at least the lowermost velocity sensor is proportional to the depth of silt, and calculating the depth of silt based on the flow velocity of said at least the lowermost velocity sensor at a selected total flow and said relationship.

In yet a further embodiment there is provided a method of measuring the flow rate of fluid in a pipe or open channel of a fluid flow network, said pipe or open channel having a system having at least one set of vertically spaced velocity sensors to measure flow velocities at predetermined horizontal levels, said method including the steps of the previous paragraph, reducing the calculated cross-sectional area of lowermost flow layers by using the calculated depth of silt, computing the flow using the measured flow velocities and cross-sectional areas for each flow layer, and summing said flows to provide a total flow at said at least one set of vertically spaced velocity sensors.

BRIEF DESCRIPTION OF THE DRAWINGS

The structure and functional features of a preferred embodiment of the present invention will become more apparent from the following detailed description when taken in conjunction with the accompanying drawings, in which.

DESCRIPTION OF THE PREFERRED EMBODIMENT

The preferred embodiment is an enhancement of the invention disclosed in International Patent Application No. PCT/AU2010/001052. In order to reduce repetition of description, the whole contents of International Patent Application No. PCT/AU2010/001052 (published as WO 2011/020143) are herein incorporated into this specification. The present invention can be used with any one of the embodiments shown in FIGS. 1 to 25 and 28 to 47 of International Patent Application No. PCT/AU2010/001052. The velocity sensors used are preferably pairs of acoustic sensors as disclosed in the PCT specification. Other sensors may be used, for example, electromagnetic sensors with electrodes set at various heights in the pipe or channel. The type of sensor is not critical but it must measure the fluid velocity accurately.

Figure 7:
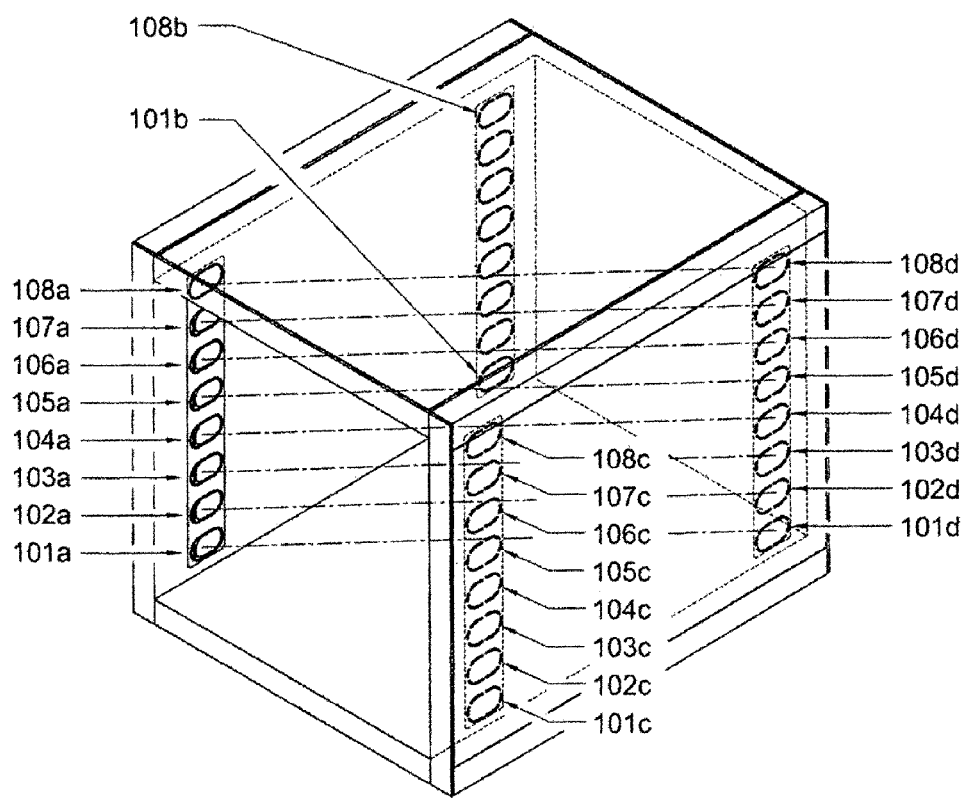
FIG. 7 is an isometric view of a preferred embodiment of the flow measurement system detailed in our International Patent Application No. PCT/AU2010/001052. This preferred embodiment is a square-section meter assembly featuring eight horizontal planes of velocity measurement.

FIG. 7 is a perspective view of a preferred embodiment of the flow measurement system 100. This preferred embodiment is a square-section meter assembly, featuring eight horizontal planes of velocity measurement, numbered 101 through 108. Any number of horizontal measurement planes may be used in this invention, from a minimum of two measurement planes to as many measurement planes as may be practicably incorporated into the meter assembly. FIG. 7 shows eight (8) velocity sensors V1 to V8 (FIG. 8) but the invention is not limited to that number. The number of velocity sensors can be increased or decreased depending on the environment where flow measurement is required.

Figure 8:
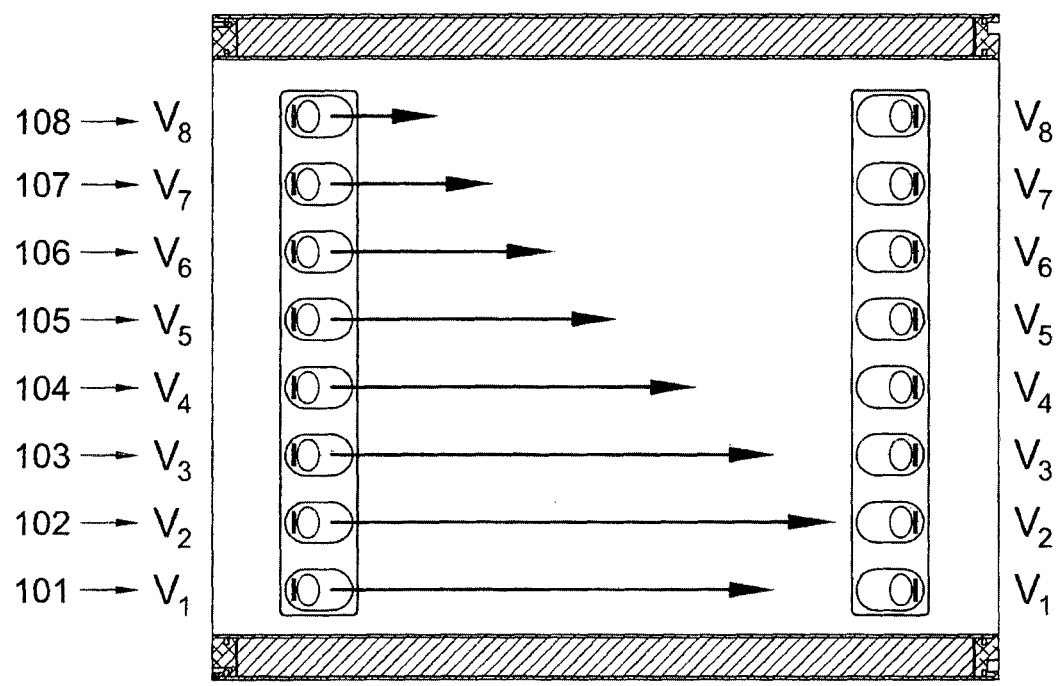
FIG. 8 is a side section view of the meter assembly referred to in FIG. 7 showing eight horizontal planes of velocity measurement.

FIG. 8 is a side section view of the meter assembly of FIG. 7 showing eight horizontal planes of velocity measurement, 101-108. Within each measurement plane 101-108 there is a velocity measurement sensor, comprising four acoustic transducers within each plane. These transducers cooperate to provide a cross-path acoustic transit time velocity measurement within their horizontal plane, as detailed in International Patent Application No. PCT/AU2010/001052. In the preferred embodiment, each plane contains four acoustic transducers, however any number of transducers could be used as is practicable.

Figure 9:
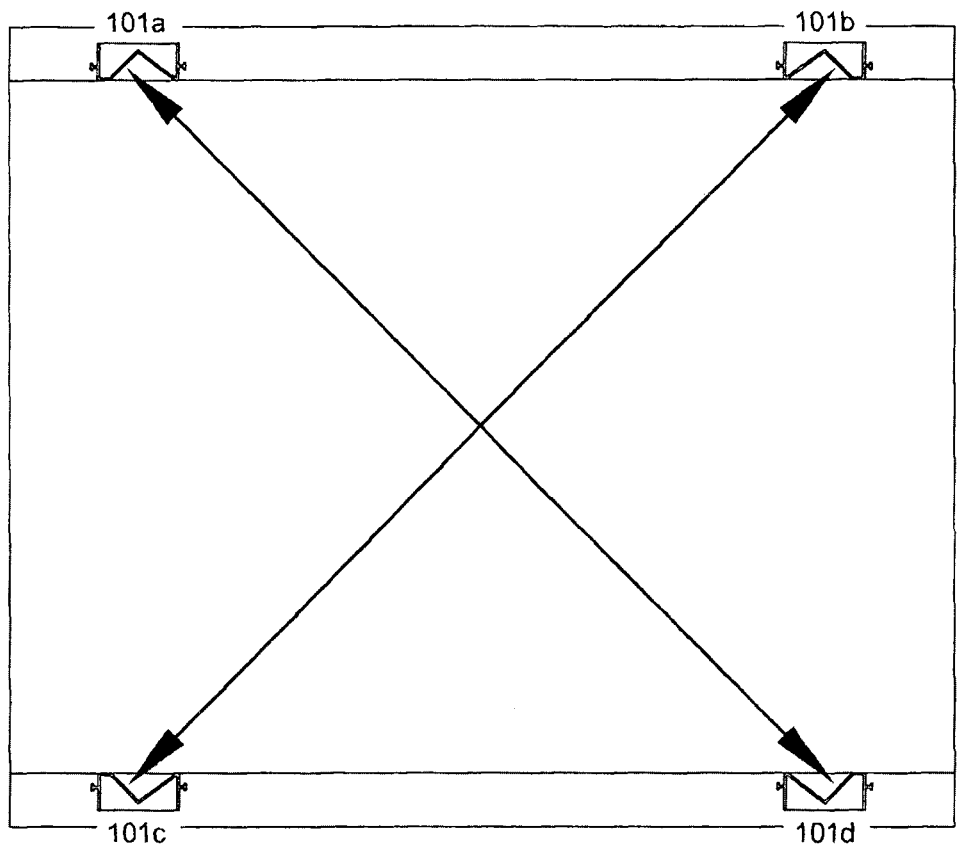
FIG. 9 is a plan section view of the meter assembly referred to in FIG. 7, showing the cross-path acoustic transit measurement technique used to determine the average velocity within each horizontal velocity measurement plane of the flow meter.

FIG. 9 is a plan section view of the meter assembly referred to in FIG. 7, showing the cross-path acoustic transit measurement plane 101. It can be seen that there are four transducers in this plane, labeled 101a, 101b, 101c, 101d. These transducers are used to measure the average flow velocity within the measurement plane as detailed in the PCT Application No. PCT/AU2010/001052.

Figure 1:
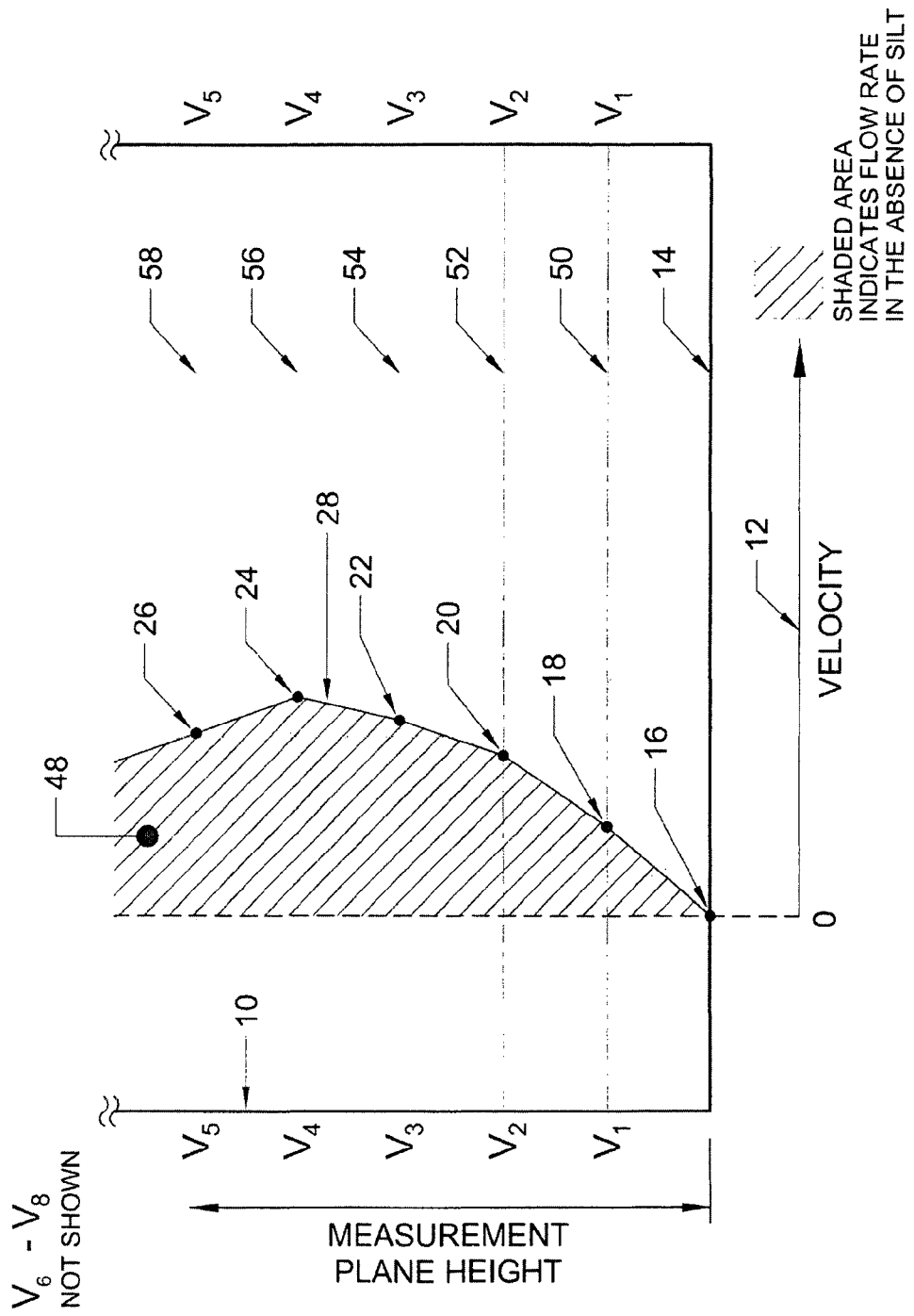
FIG. 1 is a graphical representation of the depth of the pipe or channel against the velocity detected by respective velocity sensors at differing heights in the pipe or channel with no silt present in the pipe or channel.

FIG. 1 is a graphical representation of the velocities measured within each of the velocity measurement planes 101-108. Note that this view only shows the bottom five measurement planes 101-105. The elevation of each velocity measurement plane is plotted on the y axis 10, and the velocity measured within each respective plane is plotted on the x-axis 12. FIG. 1 shows a typical velocity profile within the flow meter when there is no silt present on the bottom or base 14 of the meter (or the pipe or channel into which it is installed). It is a known scientific fact that the velocity at boundary layers is zero i.e. at the bottom or base 14 and the top (not shown) for a pipe. This is readily seen at point 16. The velocity will increase at distances offset from the boundary.

The graph shows the velocities 18 to 26 sensed within respective measurement planes V1 to V5 and the resulting plot or curve 28 is shown. The system provides a multi-path analysis of velocity across the pipe or channel at a number of horizontal layers 50 to 58. The method of computing flow is to first compute the flow (velocity multiplied by cross sectional area) for each discrete layer. The flow through the pipe or channel is therefore the sum of each discrete flow layer. The area resulting from the integration of these velocity samples (the shaded region 48) is equal to the flow passing through the system per unit width of the meter. Such a calculation, using multiple sensors V1 to V8 provides an accurate determination of flow.

Figure 2:
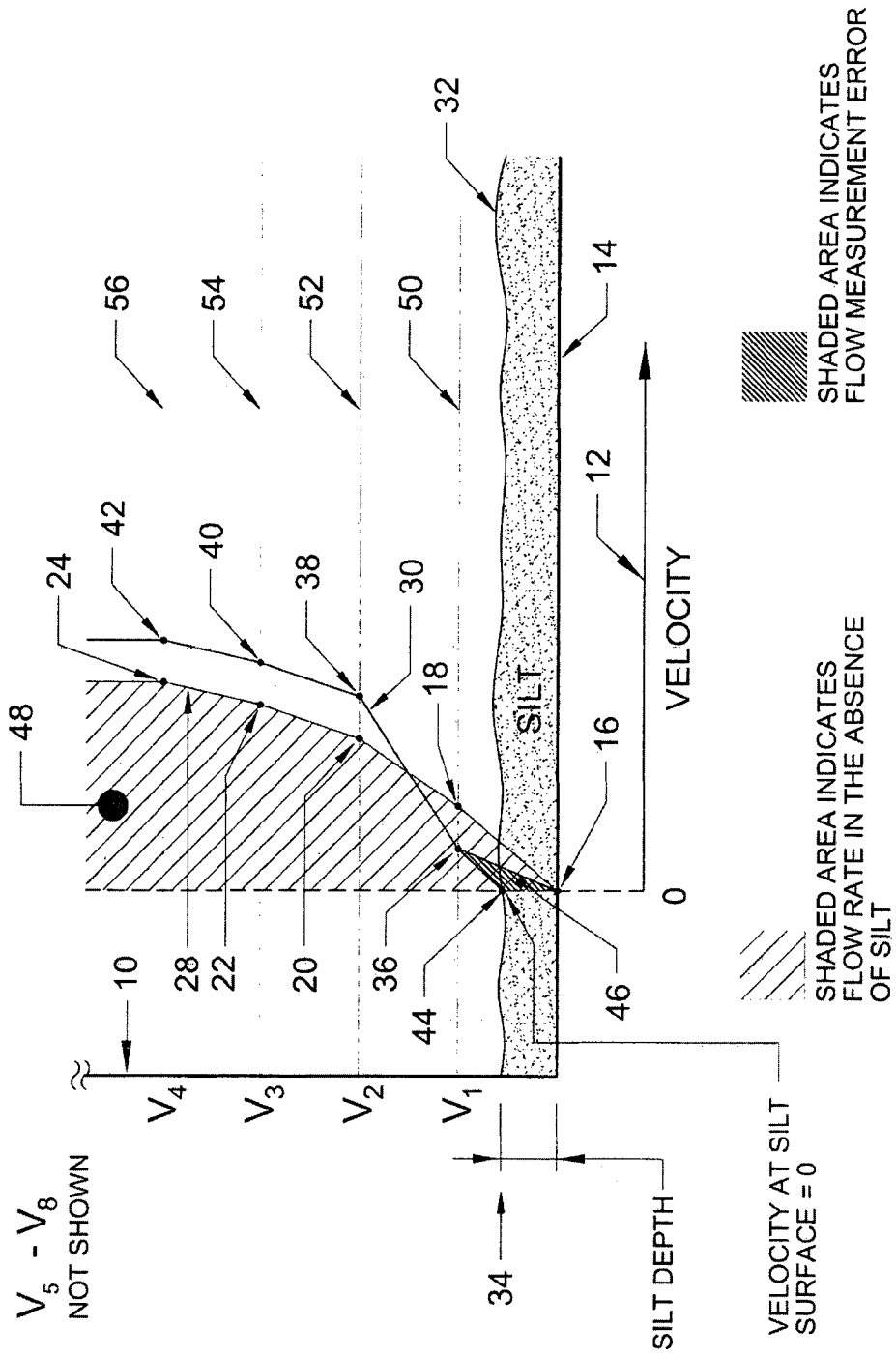
FIG. 2 is a similar graphical representation to that shown in FIG. 1 but includes the additional graph showing the effects of a layer of silt in the pipe or channel.

FIG. 2 is a similar graph to that of FIG. 1 but has an overlay plot or curve 30 resulting from a layer of silt at a depth 34. The velocities are measured by the sensors V1 to V4 and the velocities are shown as points 36 to 42. The graph illustrates the effect on the velocities at the same flow rate in the presence of silt 32. The velocity at point 36 for sensor V1 has been reduced whereas the velocities at points 38 to 42 have increased to compensate. The system extrapolates the velocity measured in the plane of sensor V1 down to the known zero velocity 16 on the floor 14 of the flow meter or channel or pipe. This extrapolation in the absence of silt is shown by the line connecting the points 18 and 16. The extrapolation in the presence of silt is shown by the line connecting the points 36 and 16. Because the flow velocity at and below the silt depth 34 is zero, the extrapolation will over-estimate the mean velocity below the bottom measurement plane. It is not known that the silt 32 is present and so it is not known that the velocity at and below elevation 34 is equal to zero. The error in velocity extrapolation and flow measurement is indicated by the shaded area 46 encompassed by lines joining point 16 to 44 (depth of silt), joining point 44 to 36, and joining point 36 to 16. The error is bounded in that the deeper the silt the smaller the velocity measured on plane V1 and hence the smaller the area of error; and conversely the shallower the silt the smaller the area of error. Accordingly, the detection of any ongoing reduction in the flow velocity of sensor V1 at a selected total flow will provide an indication of a buildup of silt in said pipe or open channel. The flow measurement accuracy is still maintained as the silt builds up. The device naturally compensates for this because of the method of measuring flow i.e. computing the flow for each individual layer, rather than traditional techniques of obtaining the average velocity for the whole cross section and then multiplying by the total area. As the silt builds up the flow through the bottom layer reduces and therefore any error associated with that measurement is also reduced. If the silt covers sensor V1 the system will still provide an accurate measurement of flow.

Flow disturbance tests have confirmed that the system maintains accuracy for this type of disturbance resulting from silt. The installation of a 25% by meter depth silt layer at the floor of the system allowed accuracy to be maintained under these conditions. Importantly, this same principle holds regardless of how many measurement planes are covered by silt or other obstructions. This method of flow measurement can be in combination with or without a gate.

Figure 3:
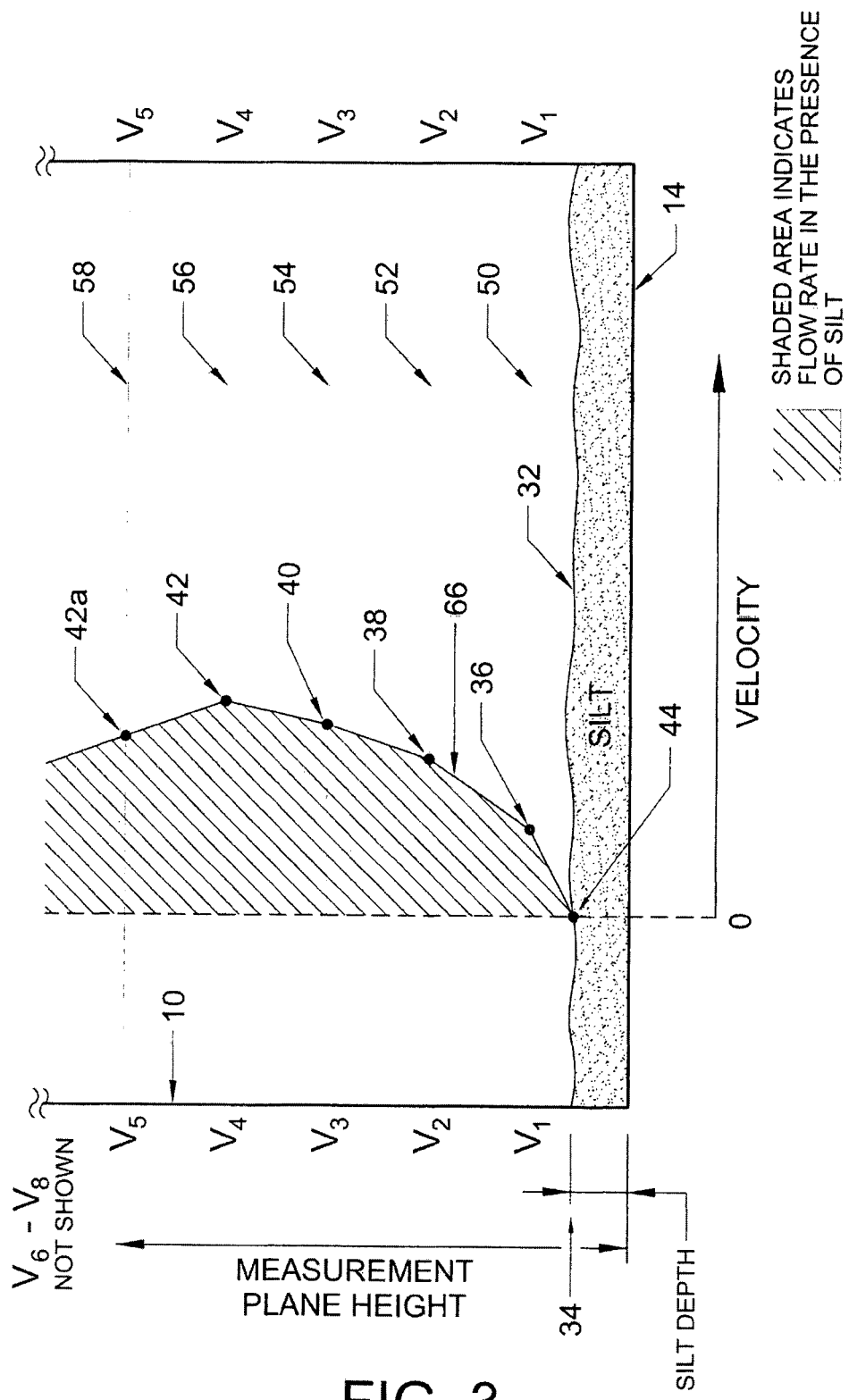
FIG. 3 is a similar graphical representation to that shown in FIG. 1 showing the correction made by an aspect of the invention where the graph has been corrected for the presence of the silt layer.
Figure 4:
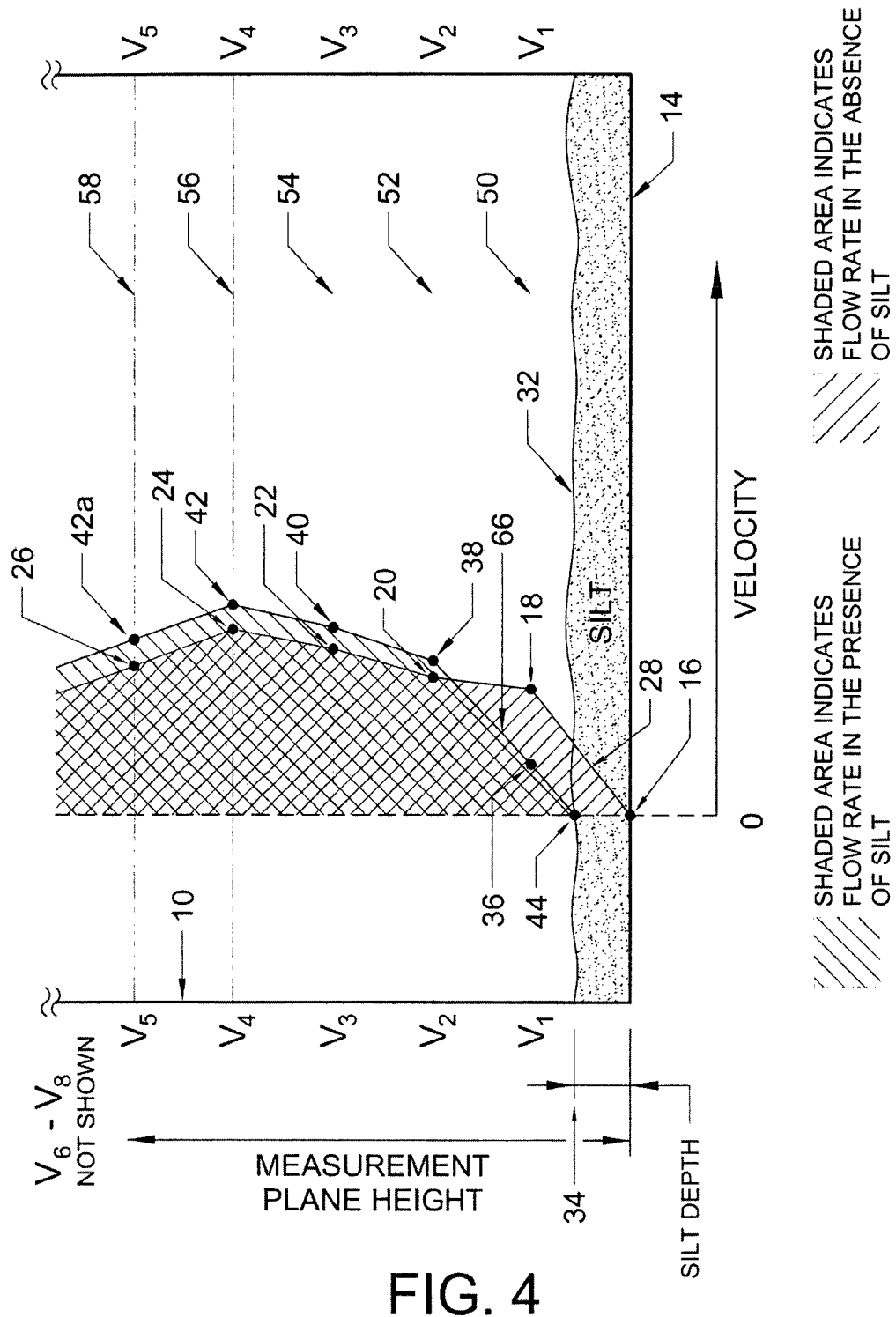
FIG. 4 is a combination of the graphs shown in FIGS. 1 and 3.
Figure 5:
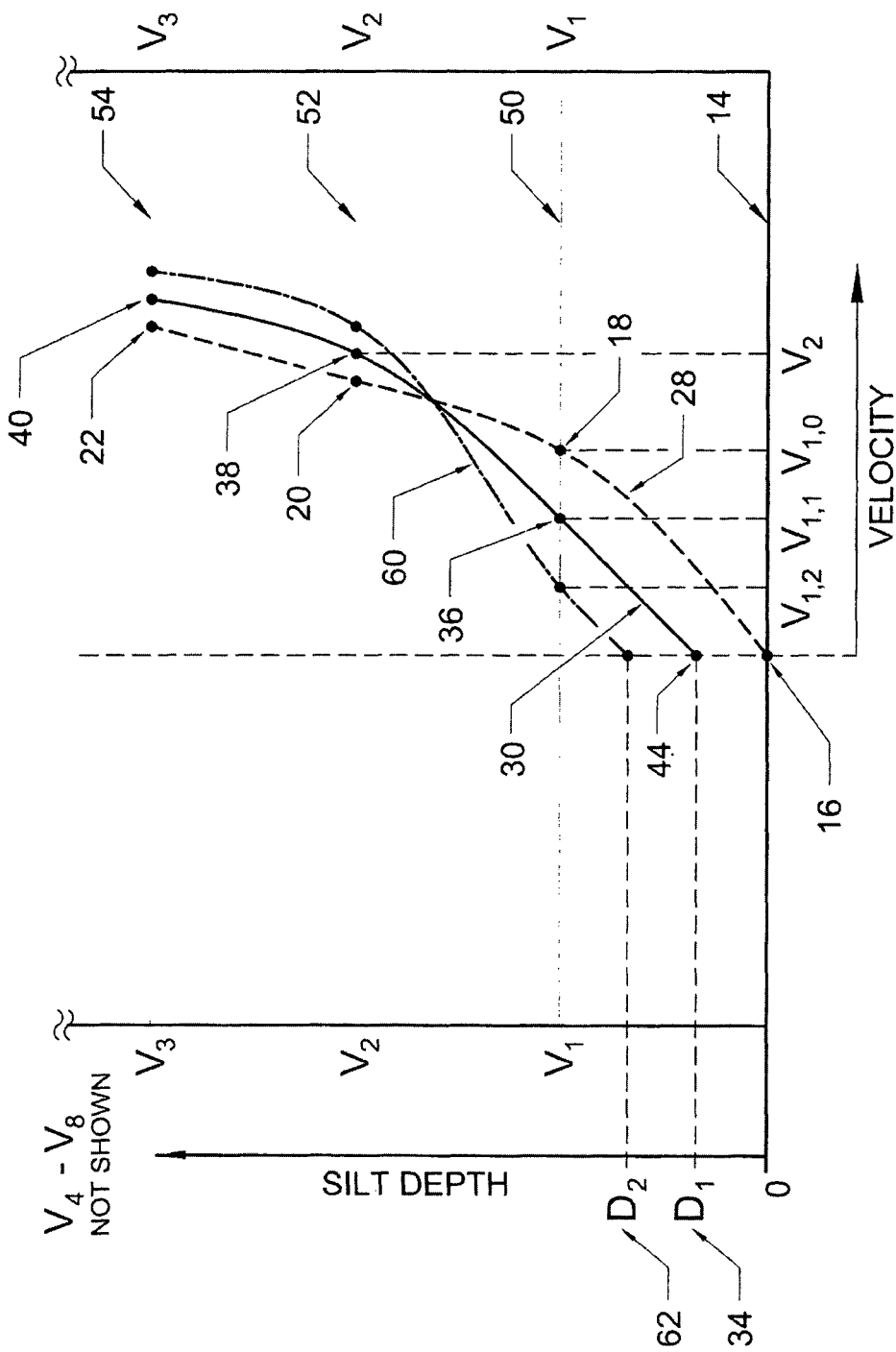
FIG. 5 is a similar graphical representation to that shown in FIG. 2 but showing the effects of the silt at differing silt depths.
Figure 6:
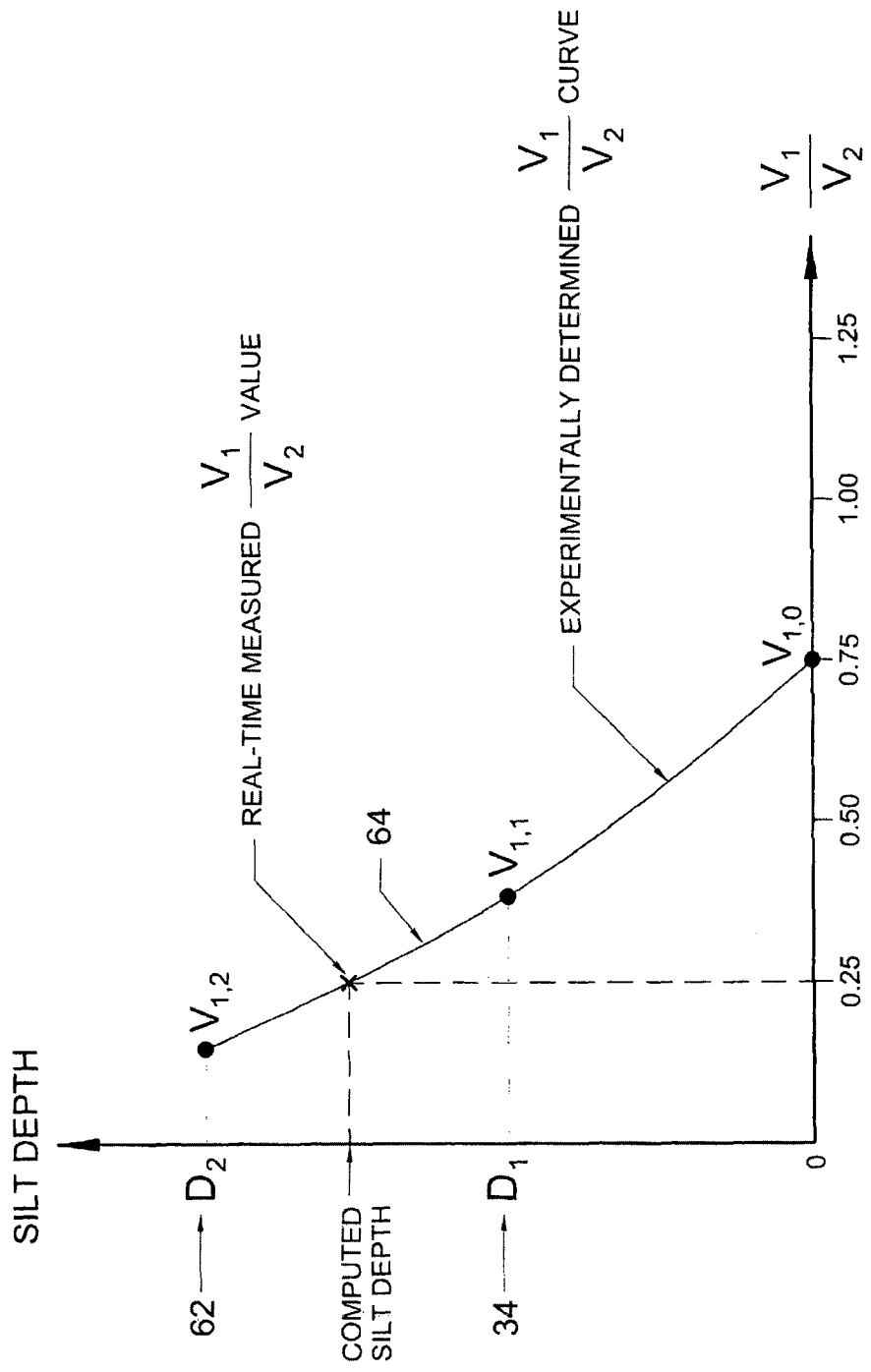
FIG. 6 is a graphical representation of the silt depth calculation curve of the computed silt depth against the division of the velocity of the lowermost sensor by the velocity of the higher adjacent sensor to the lowermost sensor to allow determination of the silt depth according to another aspect of the invention.

The above embodiment shown in FIGS. 1 and 2 allows the detection of silt and provides a system that maintains a fair degree of accuracy under varying silt depths. In order to further increase the accuracy of the system the depth of silt must be calculated. In order to reduce repetition of description the same reference numerals have been used in FIGS. 3 to 5 for similar integers in FIGS. 1 and 2. The system uses the bottom path velocity 36 measured by sensor V1 to determine the depth of silt 34 which has accumulated on the floor 14 of the system. We are assuming that sensor V1 is not covered by silt. If sensor V1 is covered by silt then sensor V2 would be used to calculate the depth of silt. The system velocity profile under silt-free conditions is known as a result of a master calibration and is shown in FIG. 4 as curve 28. The effect of silt is to reduce the bottom path velocity below its value observed under silt-free conditions 18 to a reduced value 36 as shown in FIG. 2. The reduction in bottom path velocity at sensor V1 is proportional to the depth of silt on the floor 14 of the system. By comparing the velocity measured on the bottom path 50 to the velocities measured on paths 52 to 58 of the system, the deviation of bottom velocity 36 resulting from silt build up is determined. FIG. 5 shows the calibration required by showing the velocities measured at zero depth of silt by curve 28, curve 30 at depth 34 and curve 60 at depth 62. From these calibrations it has been determined that the silt depth can be plotted against the sensor velocities of the ratio V1/V2 of the lowermost sensor V1 to the adjacent sensor V2 to provide the curve 64 shown in FIG. 6. From the graph shown in FIG. 6 the curve 64 allows the calculation of any depth of silt using the measurements of the sensor velocities V1 and V2. A relationship has thus been determined between the reduction in bottom path velocity and depth of silt. This relationship is known to hold approximately constant across the full range of flow rates that the system operates under.

If silt has covered the bottom velocity sensor V1, then the silt detection algorithm operates by comparing the velocity measured by sensor V2 to that measured by V3. Likewise, if the velocity sensor V2 is covered by silt then the silt detection algorithm operates by comparing the velocity measured by sensor V3 to that measured by sensor V4. Silt causes a null-read or a zero velocity measurement to be recorded by velocity sensors which are buried below silt, and this fact is used to identify which velocity sensors are buried below silt. The silt detection algorithm measures the depth of silt above the highest buried velocity sensor by comparing the ratio of the velocity measurements of the two velocity sensors located above the highest buried velocity sensor.

Given measurement of the reduction in the bottom path velocity, the depth of silt is calculated. The floor 14 of the system is then set equal to this silt depth, and the velocity integration is only performed down to this silt depth floor. This means that only the area of flow is integrated, and the zero flow silt region is excluded from the velocity integral. Hence the system detects the depth of silt and integrates the velocity profile from the internal ceiling of the system down to the silt floor 32. This integration provides a highly accurate measurement of fluid flow passing through the system. The system accordingly has a flow measurement accuracy unaffected by silt. FIG. 3 graphically shows the integrated curve 66 based on point 44 being shifted to the depth 34 of silt at the level of the silt.

FIG. 4 graphically illustrates the curve 66 of FIG. 3 compared with the silt-free curve 28 of FIG. 1. The detection of silt in the embodiments of FIGS. 1 to 6 can also allow a silt alarm to be incorporated into the system. An alarm can be activated by a predetermined level of silt to warn operators of the buildup of silt. Operators could then take action to remove the silt under a maintenance regime.

The invention will be understood to embrace many further modifications as will be readily apparent to persons skilled in the art and which will be deemed to reside within the broad scope and ambit of the invention, there having been set forth herein only the broad nature of the invention and certain specific embodiments by way of example.

The invention claimed is:

1. A method of detecting a buildup of silt in a pipe or open channel of a fluid flow network, said pipe or open channel having a system having at least one set of velocity sensors to measure flow velocities at predetermined horizontal levels, said method including the steps of:
   computing the flow using the measured flow velocities and cross-sectional areas for each flow layer, and summing said flows to provide a total flow,
   monitoring said measured flow velocities, and
   storing said flow velocities to detect any ongoing reduction in the flow velocity of at least the lowermost velocity sensor to provide an indication of a buildup of silt in said pipe or open channel.

2. A method of measuring flow rate of fluid in a pipe or open channel of a fluid flow network, said pipe or open channel having a system having at least one set of vertically spaced velocity sensors to measure flow velocities at predetermined horizontal levels, said method including the steps of:
   monitoring measured flow velocities;
   storing said measured flow velocities;
   calibrating said system to provide a silt-free velocity profile of said at least one set of vertically spaced velocity sensors and a plurality of velocity profiles at predetermined silt depths to allow a relationship to be calculated between silt depth and flow velocity of at least a lowermost velocity sensor at an observed velocity profile;
   applying said relationship to the flow velocity of said at least the lowermost velocity sensor to calculate a depth of silt;

reducing a calculated cross-sectional area of lowermost flow layers by using the calculated depth of silt;

computing flow using the measured flow velocities and cross-sectional areas for each flow layer; and summing said flows to provide a total flow at said at least one set of vertically spaced velocity sensors.

3. The method of claim 1 or claim 2, wherein the method is performed in a system that detects a depth of silt and integrates a velocity profile from an internal ceiling of the system down to a silt floor.

4. The method of claim 3, wherein the system has a flow measurement accuracy unaffected by silt.

5. The method of claim 3, wherein a silt alarm is incorporated into the system.

6. The method of claim 3, wherein the system comprises a square-section meter assembly featuring eight horizontal planes of velocity measurement.

7. The method of claim 1 or claim 2, wherein an alarm can be activated by a predetermined level of silt to warn operators of a buildup of silt.

8. The method of claim 1 or claim 2, wherein silt causes a null-read or a zero velocity measurement to be recorded by velocity sensors which are buried below silt, and this fact is used to identify which velocity sensors are buried below silt.

9. The method of claim 2, wherein the at least one set of vertically spaced velocity sensors comprise acoustic transducers.

10. The method of claim 9, wherein the acoustic transducers cooperate to provide a cross-path acoustic transit time velocity measurement within their horizontal plane.

* * * * *